(12) United States Patent
Kurunczi (10) Patent No.: US 8,092,643 B2
(45) Date of Patent: Jan. 10, 2012

(54) METHOD AND APPARATUS FOR CLEANING AND SURFACE CONDITIONING OBJECTS USING PLASMA

(75) Inventor: Peter Frank Kurunczi, Beverly, MA (US)

(73) Assignee: IonField Systems, LLC, Moorestown, NJ (US)

( * ) Notice: Subject to any disclaimer, the term of this patent is extended or adjusted under 35 U.S.C. 154(b) by 1232 days.

(21) Appl. No.: 11/142,988

(22) Filed: Jun. 2, 2005

(65) Prior Publication Data
US 2006/0272673 A1    Dec. 7, 2006

Related U.S. Application Data

(60) Continuation-in-part of application No. 11/143,083, filed on Jun. 2, 2005, now abandoned, which is a continuation-in-part of application No. 11/143,552, filed on Jun. 2, 2005, which is a continuation-in-part of application No. 11/043,787, filed on Jan. 26, 2005, now abandoned, which is a continuation-in-part of application No. 11/040,222, filed on Jan. 21, 2005, now abandoned, which is a continuation-in-part of application No. 11/039,628, filed on Jan. 20, 2005, now Pat. No. 7,017,594, which is a division of application No. 10/858,272, filed on Jun. 1, 2004, now Pat. No. 7,094,314.

(60) Provisional application No. 60/478,418, filed on Jun. 16, 2003.

(51) Int. Cl.
*B01L 3/00* (2006.01)
*C23F 1/00* (2006.01)

(52) U.S. Cl. ............... 156/345.43; 156/345.44; 422/553

(58) Field of Classification Search .............. 134/1, 1.1; 219/121.43, 121.52; 345/345.43; 156/345.43, 156/345.44; 422/551, 552, 553; 186.04
See application file for complete search history.

(56) References Cited

U.S. PATENT DOCUMENTS

| 5,099,100 A | 3/1992 | Bersin et al. |
| 5,133,986 A | 7/1992 | Blum et al. |

(Continued)

FOREIGN PATENT DOCUMENTS

EP    0 798 397 A2    10/1997

OTHER PUBLICATIONS

International Search Report mailed Nov. 30, 2006 for PCT Application No. PCT/US2006/021308.

(Continued)

*Primary Examiner* — Alexander Markoff
(74) *Attorney, Agent, or Firm* — Pepper Hamilton LLP (57) ABSTRACT

A method and apparatus for cleaning and surface conditioning objects using plasma are disclosed. One embodiment of the method discloses providing a plurality of elongated dielectric barrier members arranged adjacent each other, the elongated dielectric barrier members having electrodes coupled therein, providing a ground plane, introducing the objects proximate the elongated dielectric barrier members and the ground plane, and producing a dielectric barrier discharge to form plasma between the ground plane and the elongated dielectric barrier members for cleaning the objects. One embodiment of the apparatus for cleaning objects using plasma discloses a plurality of elongated dielectric barrier members arranged adjacent each other, a plurality of electrodes, each contained within, and extending substantially along the length of, respective ones of the elongated dielectric barrier members, and a ground plane proximate the plurality of elongated dielectric barrier members.

19 Claims, 9 Drawing Sheets

U.S. PATENT DOCUMENTS

| | | | |
|---|---|---|---|
| 5,200,158 | A | 4/1993 | Jacob |
| 5,225,659 | A | 7/1993 | Kusano et al. |
| 5,236,672 | A | 8/1993 | Nunez et al. |
| 5,262,125 | A | 11/1993 | Goodman |
| 5,286,532 | A | 2/1994 | Yoshikawa et al. |
| 5,292,396 | A | 3/1994 | Takashima et al. |
| 5,414,324 | A | 5/1995 | Roth et al. |
| 5,451,428 | A | 9/1995 | Rupp |
| 5,573,732 | A | 11/1996 | Waggener et al. |
| 5,633,424 | A | 5/1997 | Graves et al. |
| 5,686,789 | A | 11/1997 | Schoenbach et al. |
| 5,700,327 | A | 12/1997 | Babacz et al. |
| 5,741,460 | A | 4/1998 | Jacob et al. |
| 5,876,663 | A | 3/1999 | Laroussi |
| 5,895,558 | A | 4/1999 | Spence |
| 5,897,831 | A | 4/1999 | Jacob et al. |
| 5,935,339 | A | 8/1999 | Henderson et al. |
| 5,939,829 | A | 8/1999 | Schoenbach et al. |
| 5,965,093 | A | 10/1999 | Adams |
| 6,059,935 | A | 5/2000 | Spence |
| 6,072,273 | A | 6/2000 | Schoenbach et al. |
| 6,105,589 | A | 8/2000 | Vane |
| 6,174,500 | B1 | 1/2001 | Uno et al. |
| 6,204,605 | B1 | 3/2001 | Laroussi et al. |
| 6,225,659 | B1 | 5/2001 | Liu |
| 6,283,130 | B1 | 9/2001 | Tamura |
| 6,342,187 | B1 | 1/2002 | Jacob et al. |
| 6,346,770 | B1 | 2/2002 | Schoenbach et al. |
| 6,403,029 | B1 | 6/2002 | Schmidt |
| 6,482,369 | B2 | 11/2002 | Wang |
| 6,518,692 | B2 | 2/2003 | Schoenbach et al. |
| 6,528,022 | B1 | 3/2003 | Kinoshita |
| 6,610,257 | B2 | 8/2003 | Vane |
| 6,624,413 | B1 | 9/2003 | Klein |
| 6,632,323 | B2 * | 10/2003 | Kim et al. ............... 156/345.43 |
| 6,645,441 | B1 | 11/2003 | Andrews et al. |
| 6,652,816 | B2 | 11/2003 | Hwang |
| 6,666,928 | B2 | 12/2003 | Worm |
| 6,667,007 | B1 | 12/2003 | Schmidt |
| 6,692,704 | B2 | 2/2004 | Nelson et al. |
| 6,724,608 | B2 | 4/2004 | Hensley et al. |
| 6,784,424 | B1 | 8/2004 | Willoughby et al. |
| 6,818,193 | B2 | 11/2004 | Christodoulatos et al. |
| 6,977,722 | B2 * | 12/2005 | Wohlstadter et al. ......... 356/246 |
| 2001/0031234 | A1 | 10/2001 | Christodoulatos et al. |
| 2002/0020691 | A1 | 2/2002 | Jewett et al. |
| 2002/0036461 | A1 | 3/2002 | Schoenbach et al. |
| 2002/0076369 | A1 | 6/2002 | Hwang |
| 2002/0076370 | A1 | 6/2002 | Wong et al. |
| 2002/0124867 | A1 | 9/2002 | Kim et al. |
| 2002/0153241 | A1 | 10/2002 | Niv et al. |
| 2002/0195950 | A1 | 12/2002 | Mikhael et al. |
| 2003/0015415 | A1 | 1/2003 | Platt, Jr. et al. |
| 2003/0052096 | A1 | 3/2003 | Crowe et al. |
| 2003/0072675 | A1 | 4/2003 | Takeda et al. |
| 2003/0098230 | A1 | 5/2003 | Carlow et al. |
| 2003/0106788 | A1 | 6/2003 | Babko-Malyi |
| 2003/0113479 | A1 * | 6/2003 | Fukuda et al. ............... 427/569 |
| 2003/0116541 | A1 | 6/2003 | Chiou et al. |
| 2003/0129107 | A1 | 7/2003 | Denes et al. |
| 2003/0132100 | A1 | 7/2003 | Crowe et al. |
| 2003/0155332 | A1 | 8/2003 | Datta et al. |
| 2004/0011764 | A1 | 1/2004 | DeVries et al. |
| 2004/0022945 | A1 | 2/2004 | Goodwin et al. |
| 2004/0037756 | A1 | 2/2004 | Houston, Jr. et al. |
| 2004/0045806 | A1 | 3/2004 | Neff et al. |
| 2004/0050685 | A1 | 3/2004 | Yara et al. |
| 2004/0052028 | A1 | 3/2004 | O'Reilly et al. |
| 2004/0112537 | A1 | 6/2004 | Yamazaki et al. |
| 2004/0134890 | A1 | 7/2004 | Uhm et al. |
| 2004/0148860 | A1 | 8/2004 | Fletcher |
| 2004/0185396 | A1 | 9/2004 | Rosocha et al. |
| 2004/0195088 | A1 | 10/2004 | Rostaing et al. |
| 2004/0231926 | A1 | 11/2004 | Sakhrani et al. |
| 2004/0238124 | A1 | 12/2004 | Nakamura |

OTHER PUBLICATIONS

International Search Report mailed Nov. 30, 2006 for PCT International Application No. PCT/US2006/021309.

Written Opinion mailed Nov. 30, 2006 for PCT Application No. PCT/US2006/021308.

Written Opinion mailed Nov. 30, 2006 for PCT International Application No. PCT/US2006/021309.

U. Kogelschatz, "Dielectric-Barrier Discharges: Their History, Discharge Physics and Industrial Applications," Plasma Chemistry and Plasma Processing, vol. 23, No. 1, Mar. 2003.

U. Kogelschatz, "Filamentary, Patterned and Diffuse Barrier Discharges," IEEE Transactions on Plasma Science, vol. 30, No. 4, Aug. 2002.

N. St. J. Braithwaite, "Introduction to Gas Discharges" Plasma Sources Science and Technology, vol. 9, 2000, p. 517-527.

U. Kogelschatz et al. "Dielectric-Barrier Discharges, Principles and Applications" J. Phys IV France, 7, 1997, C4-47.

E. M. Van Veldhuizen, W.R. Rutgers. "Corona Discharges: Fundamentals and Diagnostics" Invited Paper, Proceedings of Frontiers in Low Temperature Plasma Diagnostics IV, Rolduc, The Netherlands, Mar. 2001, pp. 40-49.

Publication ANSI/SBS Apr. 2004, "Well Positions for Microplates," Jan. 2004, The Society for Biomolecular Screening, www.sbsonline.com.

H. Conrads et al., "Plasma Generation and Plasma Sources" Plasma Sources Science and Technology, vol. 9, 2000, p. 441-454.

PCT International Preliminary Report on Patentability mailed Jan. 5, 2006 for PCT Application No. PCT/US2004/17223.

PCT International Search Report mailed Jul. 8, 2005 for PCT Application No. PCT/US04/17223.

PCT Written Opinion of the International Searching Authority mailed Jul. 8, 2005 for PCT Application No. PCT/US04/17223.

Form PCT/ISA/220, "Notification of Transmittal of . . . " for PCT/US06/02025, mailed Sep. 12, 2007 (1 pg.).

Form PCT/ISA/210, "International Search Report" for PCT/US06/02025 mailed Sep. 12, 2007 (2 pgs.).

Form PCT/ISA/237, "Written Opinion of the International Searching Authority" for PCT/US06/02025 mailed Sep. 12, 2007 (4 pgs.).

Form PCT/ISA/220, "Notification of Transmittal of . . . " for PCT/US06/01268 mailed Jun. 1, 2007 (1 pg.).

Form PCT/ISA/210, "International Search Report" for PCT/US06/01268 mailed Jun. 1, 2007 (2 pgs.).

Form PCT/ISA/237, "Written Opinion of the International Searching Authority" for PCT/US06/01268 mailed Jun. 1, 2007 (3 pgs.).

Form PCT/ISA/220, "Notification of Transmittal of . . . " for PCT/US06/01762 mailed May 24, 2007 (1 pg.).

Form PCT/ISA/210, "International Search Report" for PCT/US06/01762 mailed May 24, 2007 (2 pgs.).

Form PCT/ISA/237, "Written Opinion of the International Searching Authority" for PCT/US06/01762 mailed May 24, 2007 (5 pgs.).

Form PCT/ISA/220, "Notification of Transmittal of . . . " for PCT/US06/02010 mailed Jun. 4, 2007 (1 pg.).

Form PCT/ISA/210, "International Search Report" mailed Jun. 4, 2007 for PCT/US06/02010 (2 pgs.).

Form PCT/ISA/237, "Written Opinion of the International Searching Authority" for PCT/US06/02010 mailed Jun. 4, 2007 (3 pgs.).

Form PCT/ISA/220, "Notification of Transmittal of . . . " for PCT/US05/42637 mailed Sep. 25, 2007 (1 pg.).

Form PCT/ISA/210, "International Search Report" for PCT/US05/42637 mailed Sep. 25, 2007 (3 pgs.).

Form PCT/ISA/237, "Written Opinion of the International Searching Authority" for PCT/US05/42637 mailed Sep. 25, 2007 (4 pgs.).

* cited by examiner

METHOD AND APPARATUS FOR CLEANING AND SURFACE CONDITIONING OBJECTS USING PLASMA

CROSS-REFERENCE TO RELATED APPLICATIONS

This application is a continuation-in-part of U.S. patent application Ser. No. 11/143,083, filed Jun. 2, 2005, which is a continuation-in-part of U.S. patent application Ser. No. 11/143,552, filed Jun. 2, 2005, which is a continuation-in-part of U.S. patent application Ser. No. 11/043,787, filed Jan. 26, 2005, which is a continuation-in-part of U.S. patent application Ser. No. 11/040,222, filed Jan. 21, 2005, which is a continuation-in-part of U.S. patent application Ser. No. 11/039,628, filed Jan. 20, 2005, which is a divisional of U.S. patent application Ser. No. 10/858,272, filed Jun. 1, 2004, which application claims the benefit of U.S. Provisional Patent Application Ser. No. 60/478,418, filed on Jun. 16, 2003, all prior applications of which are incorporated herein by reference in their entirety.

BACKGROUND OF THE INVENTION

1. Field of the Invention

Embodiments of the present invention generally relate to a method and apparatus for cleaning and surface conditioning fluid handling devices and in particular to a method and apparatus for cleaning and surface conditioning portions of fluid handling devices using plasma.

2. Description of the Related Art

In certain clinical, industrial and life science testing laboratories, extremely small quantities of fluids, for example, volumes between a drop (about 25 microliters) and a few nano-liters may need to be analyzed. Several known methods are employed to transfer these small amounts of liquid compounds from a source to a testing device. Generally, liquid is aspirated from a fluid holding device into a fluid handling device. The fluid handling device may include, but is not limited to, a probe, cannula, disposable pipette, pin tool or other similar component or plurality of such components (hereinafter collectively referred to as "probes"). The fluid handling device and its probes may move, manually, automatically or robotically, dispensing the aspirated liquid into another fluid holding device for testing purposes.

Commonly, the probes, unless disposable, are reused from one test to the next. As a result, at least the tips of the probes must be cleaned between each test. Conventionally, the probes undergo a wet "tip wash" process. That is, they are cleaned in between uses with a liquid solvent, such as Dimethyl Sulfoxide (DMSO) or simply water.

These methods and apparatus for cleaning and conditioning fluid handling devices have certain disadvantages. For example, the wet "tip wash" process takes a relatively long time and can be ineffective in cleaning the probe tips to suitable levels of cleanliness. Furthermore, disposing the used solvents from the wet process presents a challenge. Thus, there is a need for improved methods and apparatus for cleaning and surface conditioning fluid handling devices.

SUMMARY OF THE INVENTION

The present invention generally relates to an apparatus and method for cleaning at least a portion of a fluid handling device, which device includes a plurality of probes, using plasma.

In one embodiment of the present invention, there is provided an apparatus for cleaning objects using plasma, comprising a plurality of elongated dielectric barrier members arranged adjacent each other; a plurality of electrodes, each contained within, and extending substantially along the length of, respective ones of the elongated dielectric barrier members; and a ground plane proximate the plurality of elongated dielectric barrier members.

In accordance with another embodiment of the present invention, there is provided an apparatus for cleaning objects using plasma, comprising a plurality of elongated dielectric barrier members arranged adjacent each other in a microtiter plate matrix format; a plurality of electrodes, each contained within, and extending substantially along the length of, respective ones of the elongated dielectric barrier members; and a ground plane proximate the plurality of elongated dielectric barrier members.

In accordance with yet another embodiment of the present invention, there is provided a method for cleaning at least a portion of a plurality of probes, comprising providing a plurality of elongated dielectric barrier members having electrodes arranged therein; providing a ground plane proximate the plurality of elongated dielectric barrier members; introducing the probes proximate the elongated dielectric barrier members and ground plane; and generating a dielectric barrier discharge to form plasma between the elongated dielectric barrier members and ground plane for cleaning at least a portion of each of the probes.

BRIEF DESCRIPTION OF THE DRAWINGS

So the manner in which the above recited features of the present invention can be understood in detail, a more particular description of the present invention, briefly summarized above, may be had by reference to embodiments, some of which are illustrated in the appended drawings. It is to be noted; however, the appended drawings illustrate only typical embodiments of the present invention and are therefore not to be considered limiting of its scope, for the present invention may admit to other equally effective embodiments.

While embodiments of the present invention are described herein by way of example using several illustrative drawings, those skilled in the art will recognize the present invention is not limited to the embodiments or drawings described. It should be understood the drawings and the detailed description thereto are not intended to limit the present invention to the particular form disclosed, but to the contrary, the present invention is to cover all modification, equivalents and alternatives falling within the spirit and scope of embodiments of the present invention as defined by the appended claims.

The headings used herein are for organizational purposes only and are not meant to be used to limit the scope of the description or the claims. As used throughout this application, the word "can" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

The term "plasma" is used to describe a quasi-neutral gas of charged and neutral species characterized by a collective behavior governed by coulomb interactions. Plasma is typically obtained when sufficient energy, higher than the ionization energy of the neutral species, is added to the gas causing ionization and the production of ions and electrons. The energy can be in the form of an externally applied electromagnetic field, electrostatic field, or heat. The plasma becomes an electrically conducting medium in which there are roughly equal numbers of positively and negatively charged particles, produced when the atoms/molecules in a gas become ionized.

A plasma discharge is produced when an electric field of sufficient intensity is applied to a volume of gas. Free electrons are then subsequently accelerated to sufficient energies to produce electron-ion pairs through inelastic collisions. As the density of electrons increase, further inelastic electron atom/molecule collisions will result in the production of further charge carriers and a variety of other species. The species may include excited and metastable states of atoms and molecules, photons, free radicals, molecular fragments, and monomers.

The term "metastable" describes a type of atom/molecule excited to an upper electronic quantum level in which quantum mechanical selection rules forbid a spontaneous transition to a lower level. As a result, such species have long, excited lifetimes. For example, whereas excited states with quantum mechanically allowed transitions typically have lifetimes on the order of $10^{-9}$ to $10^{-8}$ seconds before relaxing and emitting a photon, metastable states can exist for about $10^{-6}$ to $10^{1}$ seconds. The long metastable lifetimes allow for a higher probability of the excited species to transfer their energies directly through a collision with another compound and result in ionization and/or dissociative processes.

The plasma species are chemically active and/or can physically modify the surface of materials and may therefore serve to form new chemical compounds and/or modify existing compounds. For example, the plasma species can modify existing compounds through ionization, dissociation, oxidation, reduction, attachment, and recombination.

A non-thermal, or non-equilibrium, plasma is one in which the temperature of the plasma electrons is higher than the temperature of the ionic and neutral species. Within atmospheric pressure non-thermal plasma, there is typically an abundance of the aforementioned energetic and reactive particles (i.e., species), such as ultraviolet photons, excited and/or metastable atoms and molecules, atomic and molecular ions, and free radicals. For example, within an air plasma, there are excited, metastable, and ionic species of $N_2$, N, $O_2$, O, free radicals such as OH, $HO_2$, NO, O, and $O_3$, and ultraviolet photons ranging in wavelengths from 200 to 400 nanometers resulting from $N_2$, NO, and OH emissions. In addition to the energetic (fast) plasma electrons, embodiments of the present invention harness and use these "other" particles to clean and surface condition portions of liquid handling devices, such as probes, and the like.

Figures 1A, 1B:
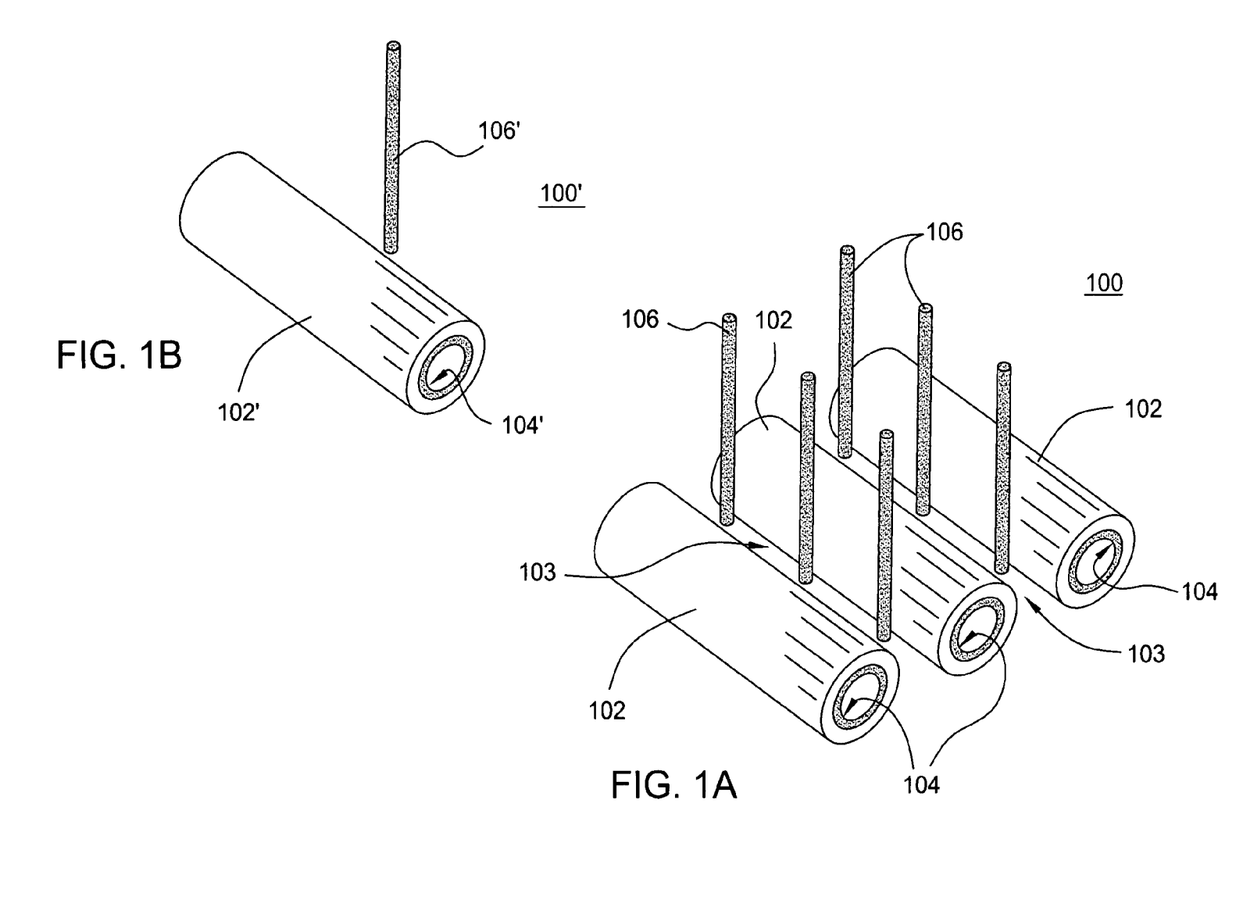
FIG. 1A is a top, partial perspective view of a plurality of conductive probes being introduced to a plurality of elongated dielectric barrier members with coupled inner electrodes in accordance with an embodiment of the present invention.
FIG. 1B is a top, partial perspective view of one conductive probe being introduced to one dielectric barrier member with a coupled inner electrode in accordance with an embodiment of the present invention.

Referring to FIG. 1A, a partial view of a non-thermal atmospheric pressure plasma cleaning device 100 in accordance with an embodiment of the present invention is disclosed. The device 100 includes a plurality of elongated dielectric barrier members 102 arranged in a matrix or array, which lie in a plane. The members 102 are substantially regularly spaced apart from each other forming a gap 103 between adjacent members 102. Each dielectric barrier member 102 includes an inner electrode 104 extending within, and substantially along the length of, respective elongated dielectric barrier members 102. A plurality of conductive probes 106 are shown extending into open spaces or gaps 103 between the plurality of dielectric barrier members 102. In one embodiment, the probes 106 are part of a fluid handling device. As such, the probes 106 are attached to and extend from a fluid handling device (not shown), which may be part of a microtiter plate test bed set up. In other embodiments, the probes 106 may be any form of a conductive element that would benefit from plasma cleaning.

The elongated dielectric barrier members 102 are made of any type of material capable of providing a surface for a dielectric barrier discharge of atmospheric pressure plasma (described herein). Dielectric barrier material useful in this embodiment of the present invention includes, but is not limited to, ceramic, glass, plastic, polymer epoxy, or a composite of one or more such materials, such as fiberglass or a ceramic filled resin (available from Cotronics Corp., Wetherill Park, Australia).

In one embodiment, a ceramic dielectric barrier is alumina or aluminum nitride. In another embodiment, a ceramic dielectric barrier is a machinable glass ceramic (available from Corning Incorporated, Corning, N.Y.). In yet another embodiment of the present invention, a glass dielectric barrier is a borosilicate glass (also available from Corning Incorporated, Corning, N.Y.). In still another embodiment, a glass dielectric barrier is quartz (available from GE Quartz, Inc., Willoughby, Ohio). In an embodiment of the present invention, a plastic dielectric barrier is polymethyl methacrylate (PLEXIGLASS and LUCITE, available from Dupont, Inc., Wilmington, Del.). In yet another embodiment of the present invention, a plastic dielectric barrier is polycarbonate (also available from Dupont, Inc., Wilmington, Del.). In yet another embodiment, a plastic dielectric barrier is a fluoropolymer (available from Dupont, Inc., Wilmington, Del.). In another embodiment, a plastic dielectric barrier is a polyimide film (KAPTON, available from Dupont, Inc., Wilmington, Del.). Dielectric barrier materials useful in the present invention typically have dielectric constants ranging between 2 and 30. For example, in one embodiment that uses a polyimide film plastic such as KAPTON, at 50% relative humidity, with a dielectric strength of 7700 Volts/mil, the film would have a dielectric constant of about 3.5.

The inner electrode 104 may comprise any conductive material, including metals, alloys and conductive compounds. In one embodiment, a metal may be used. Metals useful in this embodiment of the present invention include, but are not limited to, copper, silver, aluminum, and combinations thereof. In another embodiment of the present invention, an alloy of metals may be used as the inner electrode 104. Alloys useful in this embodiment of the present invention include, but are not limited to, stainless steel, brass, and bronze. In another embodiment of the present invention, a conductive compound may be used. Conductive compounds useful in the present invention include, but are not limited to, indium-tin-oxide.

The inner electrodes 104 of the present invention may be formed using any method known in the art. For example, in one embodiment of the present invention, the inner electrodes 104 may be formed using a foil. In another embodiment of the present invention, the inner electrodes 104 may be formed using a wire. In yet another embodiment of the present invention, the inner electrodes 104 may be formed using a solid block of conductive material. In another embodiment of the present invention, the inner electrodes 104 may be deposited as an integral layer directly onto the inner core of the dielectric barrier members 102. In one such embodiment, an inner electrode 104 may be formed using a conductive paint, which is applied to the inner core of the elongated dielectric barrier members 102. Alternative electrode designs are contemplated by embodiments of the present invention.

In one use of the present invention, the conductive probes 106 are part of the fluid handling device and are introduced in the gap 103, i.e., proximate the elongated dielectric barrier members 102 of the plasma cleaning device 100. Use of the term "probe" throughout this application is meant to include, but not be limited to, probes, cannulas, pin tools, pipettes and spray heads or any portion of a fluid handling device that is capable of carrying fluid. These portions can be generally hollow to carry the fluid but may be solid and include a surface area capable of retaining fluid. All of these different types of fluid handling portions of a fluid handling device are collectively referred to in this application as "probes." In an embodiment, the probe is conductive and is made of conductive material similar to that material described above in connection with the inner electrode 104. In other embodiments, as described below, the probe is non-conductive.

FIG. 1B depicts a non-thermal atmospheric pressure plasma cleaning device 100' in accordance with another embodiment of the present invention. In this embodiment, only one elongated dielectric barrier member 102' and one inner electrode 104' are shown. In addition, only one conductive probe 106' is introduced proximate the dielectric 102'. However, multiple elongated dielectric barrier members 102' with respective inner electrodes 104', where conductive probes 106' are introduced proximate the elongated dielectric barrier members 102' are contemplated by embodiments of the present invention.

Each conductive probe 106 may be introduced proximate one (FIG. 1B) or more (FIG. 1A) elongated dielectric barrier members 102. When each conductive probe 106 is proximate one elongated dielectric barrier member 102, the conductive probe 106 may be introduced proximate the top of the elongated dielectric barrier member 102 as best shown in FIG. 1B. When each conductive probe 106 is introduced proximate two elongated dielectric barrier members 102, the conductive probe 106 may be introduced proximate or between the two elongated dielectric barrier members 102, as best shown in FIG. 1A.

Figure 2:
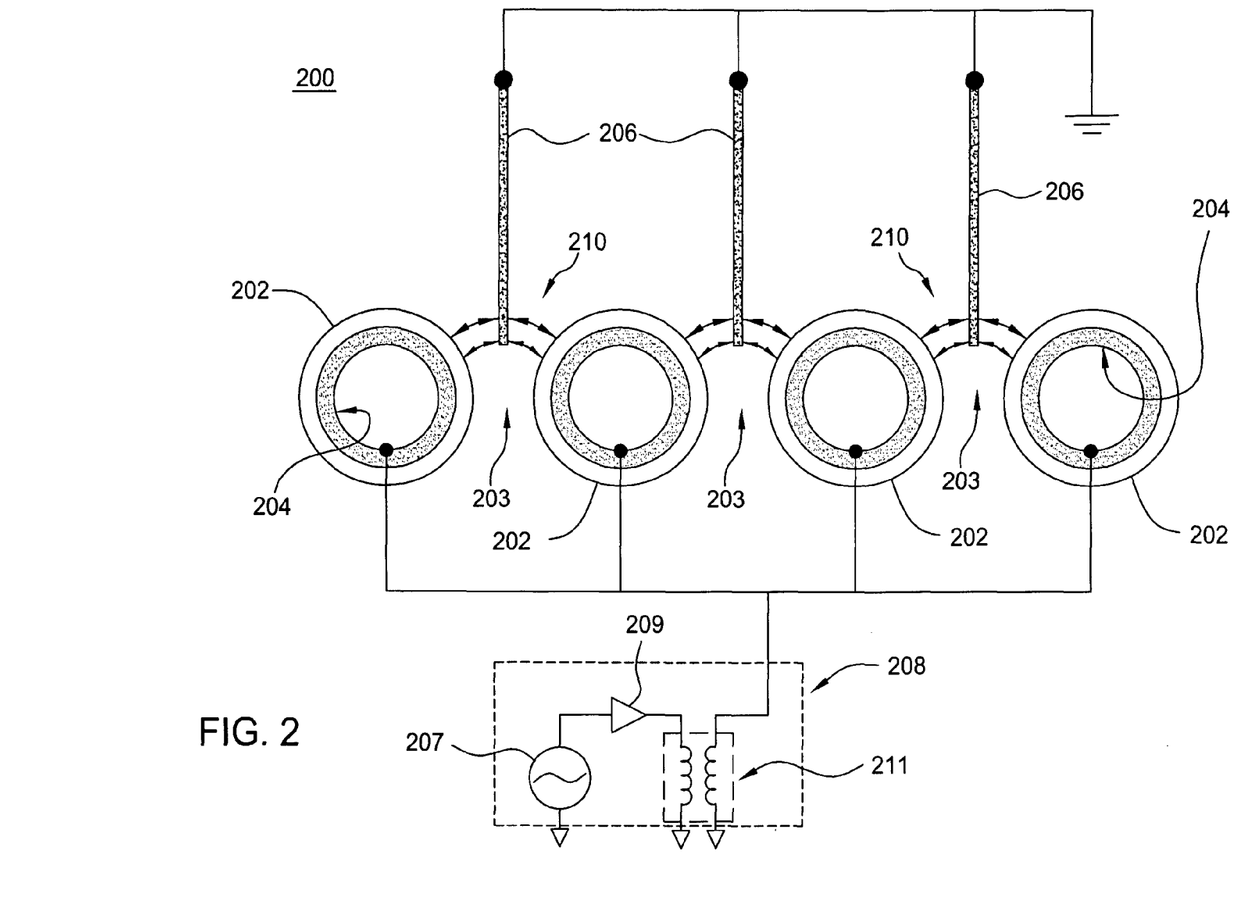
FIG. 2 is a front, expanded view of the device and the conductive probes of FIG. 1A showing the components electrically coupled.

Referring to FIG. 2, a portion of an atmospheric pressure plasma device is designated 200. This section 200 includes a plurality of inner electrodes 204 of each respective elongated dielectric barrier member 202 electrically connected to an AC voltage source 208. The conductive probes 206 are electrically grounded with respect to the AC voltage source 208. The AC voltage source 208 in this embodiment includes an AC source 207, a power amplifier 209 and a transformer 211 to supply voltage to the inner electrodes 204.

In certain embodiments of the atmospheric pressure plasma device 200, a dielectric barrier discharge (DBD) (also known as a "silent discharge") technique is used to create microdischarges of atmospheric pressure plasma. In a DBD technique, a sinusoidal voltage from an AC source 207 is applied to at least one inner electrode 204, within an insulating dielectric barrier member 202. Dielectric barrier discharge techniques have been described in "Dielectric-barrier Discharges: Their History, Discharge Physics, and Industrial Applications", Plasma Chemistry and Plasma Processing, Vol. 23, No. 1, March 2003, and "Filamentary, Patterned, and Diffuse Barrier Discharges", IEEE Transactions on Plasma Science, Vol. 30, No. 4, Aug. 2002, both authored by U. Kogelschatz, the entire disclosures of which are incorporated by reference herein.

In short, to obtain a substantially uniform atmospheric pressure plasma in air, a dielectric barrier is placed in between the electrode 204 and the conductive probe 206 to control the discharge, i.e., choke the production of atmospheric pressure plasma. That is, before the discharge can become an arc, the dielectric barrier 202 chokes the production of the discharge. Because this embodiment is operated using an AC voltage source, the discharge oscillates in a sinusoidal cycle. The microdischarges occur near the peak of each sinusoid. One advantage to this embodiment is that controlled non-equilibrium plasmas can be generated at atmospheric pressure using a relatively simple and efficient technique.

In operation, the AC voltage source 208 applies a sinusoidal voltage to the inner electrodes 204. Then, the plurality of conductive probes 206 are introduced into the gap 203 between adjacent elongated dielectric barriers 202. A dielectric barrier discharge (DBD) is produced. This DBD forms atmospheric pressure plasma, represented by arrows 210. In an embodiment of the present invention, atmospheric pressure plasma is obtained when, during one phase of the applied AC voltage, charges accumulate between the dielectric surface and the opposing electrode until the electric field is sufficiently high enough to initiate an electrical discharge through the gas gap (also known as "gas breakdown").

During an electrical discharge, an electric field from the redistributed charge densities may oppose the applied electric field and the discharge is terminated. In one embodiment, the applied voltage-discharge termination process may be repeated at a higher voltage portion of the same phase of the applied AC voltage or during the next phase of the applied AC voltage. A point discharge generally develops within a high electric field region near the tip of the conductive probe 206.

To create the necessary DBD for an embodiment of the present invention, the AC voltage source 208 includes an AC power amplifier 209 and a high voltage transformer 211. The frequency ranges from about 10,000 Hertz to about 20,000 Hertz, sinusoidal. The power amplifier has an output voltage of from about 0 Volts (rms) to about 22.5 Volts (rms) with an output power of about 500 watts. The high voltage transformer ranges from about 0 V (rms) to 7,000 Volts (rms) (which is about 10,000 volts (peak)). Depending on the geometry and gas used for the plasma device, the applied voltages can range from about 500 to about 10,000 Volts (peak), with frequencies ranging from line frequencies of about 50 Hertz up to about 20 Megahertz.

In an embodiment of the present invention, the frequency of a power source may range from 50 Hertz up to about 20 Megahertz. In another embodiment of the present invention, the voltage and frequency may range from about 5,000 to about 15,000 Volts (peak) and about 50 Hertz to about 50,000 Hertz, respectively.

The gas used in the plasma device 200 embodiment of the present invention can be ambient air, pure oxygen, any one of the rare gases, or a combination of each such as a mixture of air or oxygen with argon and/or helium. Also, the gas may include an additive, such as hydrogen peroxide, or organic compounds such as methanol, ethanol, ethylene or isopropynol to enhance specific atmospheric pressure plasma cleaning properties.

Figure 3A:
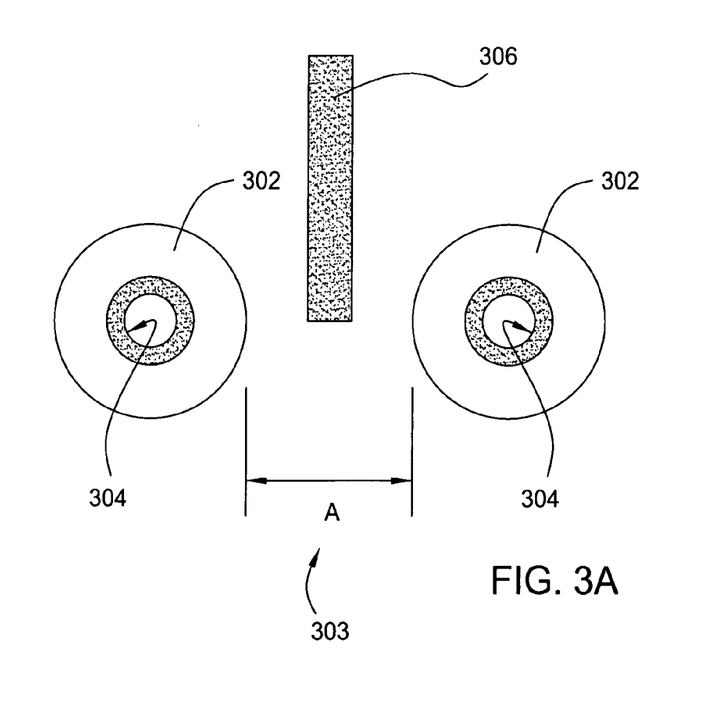
FIG. 3A is a cross sectional schematic view of the device and a conductive probe of FIG. 1A showing the dimensions and spacing among components.

FIG. 3A depicts one example of the geometry and relationship among components of one embodiment of the present invention. The elongated dielectric barrier member 302 may comprise, for example, an elongated hollow tube with a hollow inner electrode 304 extended substantially the length of the elongated dielectric barrier member 302. Alternatively, the elongated dielectric barrier member 302 may be other than a tube such as a solid with a solid inner electrode 304. The elongated dielectric barrier 302 may be formed of different shapes as well. For example, and not in any way limiting, the shape of the elongated dielectric barrier may be tubular, circular, square, rectangular, oval, polygonal, triangular, trapezoidal, rhombus and irregular. If tubular, each dielectric barrier tube is about 2 mm in diameter and about 75 to about 120 mm long.

The elongated dielectric barrier members 302 are placed adjacent one another, defining a plane. They are spaced at regular intervals and form a gap 303, designated as spacing A. Alternatively, the members 302 can be staggered in a non-planar arrangement with respect to one another. The spacing A is sized to allow at least a portion of each of the plurality of probes to be introduced proximate or between the elongated dielectric barrier members. The gap 303 or spacing A can approach zero, provided there is a sufficient gap to allow gas such as air to flow through the elongated dielectric barrier members 302. Spacing A or gap 303 can range from about 0 mm to about 10 mm. The spacing A or gap 303 may also range from about 2 mm to about 9.5 mm. In one embodiment, the spacing A is about 9 mm. In another embodiment, the spacing A is about 4.5 mm. In yet another embodiment, the spacing A is about 2.25 mm.

In an embodiment, where both the probes 306 and the plurality of elongated dielectric barrier members 302 are substantially tubular (each having substantially the same respective diameter) and the plurality of probes 306 are substantially tubular (each having substantially the same respective diameter), the probe 306 diameter is relatively smaller than the diameter of the plurality of elongated dielectric barrier members. Thus, even if the spacing A (or gap 303) between the elongated dielectric barrier members 302 approaches 0 mm, the probes 306 can be introduced proximate, if not between, a pair of elongated dielectric members 302.

Figure 3B:
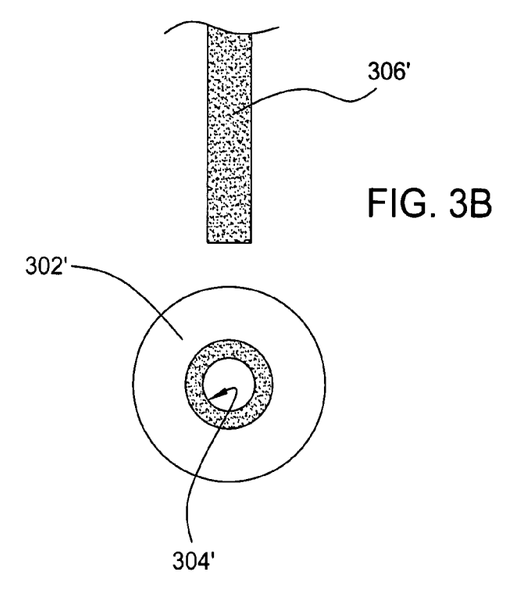
FIG. 3B is a cross sectional schematic view of the device of FIG. 1A showing a conductive probe proximate the top of a dielectric barrier member.

Alternatively, as shown in FIG. 3B, the probes 306' can be introduced generally proximate the top of each elongated dielectric barrier member 302'. FIG. 3B depicts only one probe 306' and one dielectric 302' but it is to be understood the present invention contemplates a plurality of probes 306' being introduced proximate the top of respective dielectric barrier members 302'.

Figure 4:
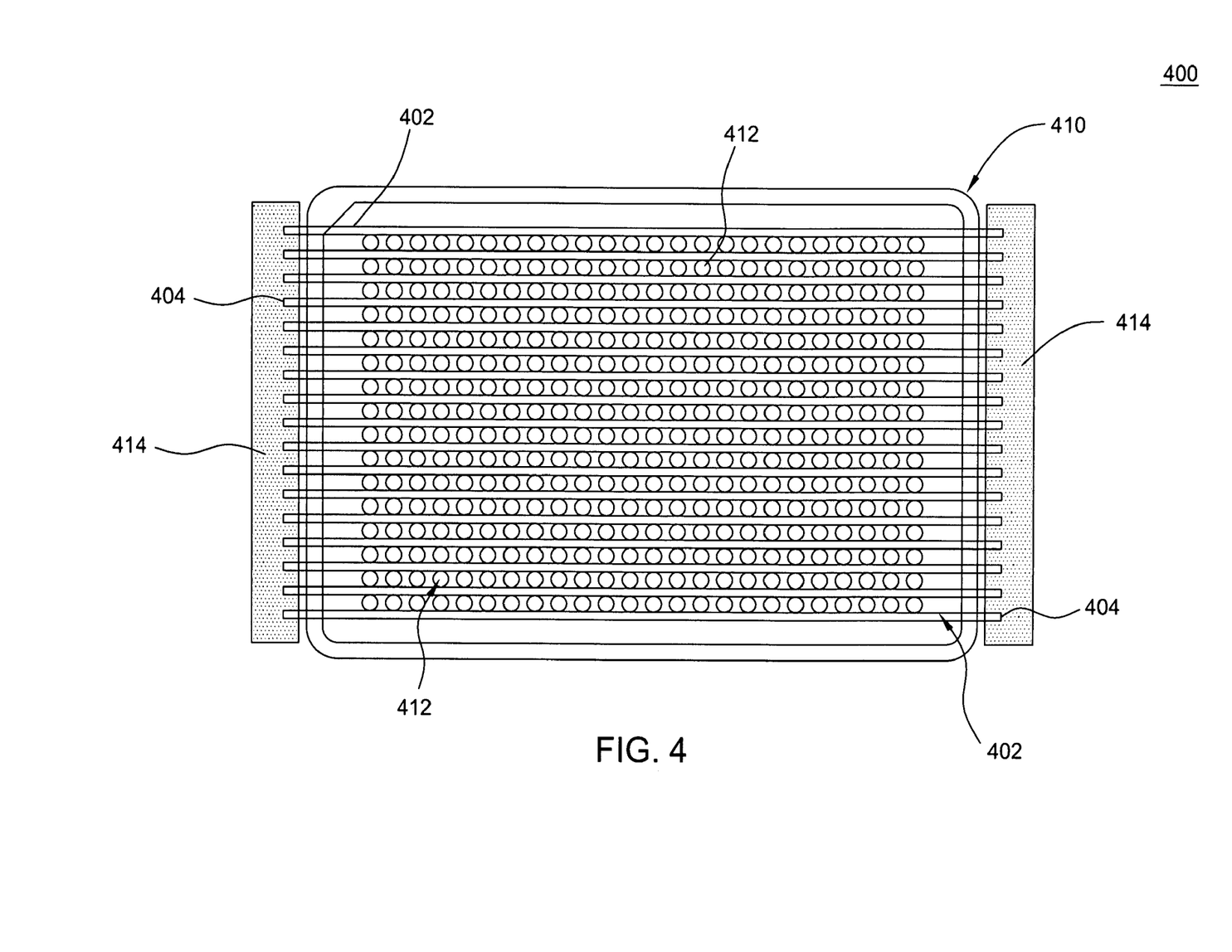
FIG. 4 is a top plan view of a matrix or array of the device of FIG. 1A showing the plurality of elongated dielectric barrier members arranged in a microtiter plate format.

Referring to FIG. 4, a top plan view of the above described plasma device configured and arranged in a standard microtiter plate format 400. For example, the microtiter plate format may be sized to accommodate about 96 openings for receiving a plurality of fluid handling probes. Alternatively, the microtiter plate is sized to accommodate about 384 openings for receiving a plurality of probes as depicted in FIG. 4. As an alternative, the wells and the pitch between rows of wells of the microtiter plate are sized to accommodate about 1536 openings for receiving a plurality of probes.

Microtiter plates or microplates, similar to the one depicted in FIG. 4, are small, usually plastic, reaction vessels. The microplate 400 has a tray or cassette 410 covered with wells or dimples 412 arranged in orderly rows. These wells 412 are used to conduct separate chemical reactions during a fluid testing step. The large number of wells, which typically number 96, 384 (as shown in FIG. 4) or 1536, depending upon the well size and pitch between rows of wells of the microplate allow for many different reactions to take place at the same time. Microplates are ideal for high-throughput screening and research. They allow miniaturization of assays and are suitable for many applications including drug testing, genetic study, and combinatorial chemistry.

The microplate 400 has been equipped with an embodiment of the present invention. Situated in rows on the top surface of the microplate 400 and between the wells 412 are a plurality of elongated dielectric barrier members 402 similar to those described hereinabove. The inner electrodes 404 of the elongated dielectric barrier members 402 are electrically coupled to the AC voltage source through bus bars or contact planes 414 of the cassette 410.

The elongated dielectric barrier members 402 are each spaced apart in this particular embodiment a pitch of about 4.5 mm. In alternative embodiments, where the well count is 96, the members 402 are spaced apart a pitch of about 9 mm. In yet another embodiment, where the wells 412 numbered 1536, the pitch is 2.25 mm. During a cleaning step, the wells 412 of the microplate 400 do not necessarily function as liquid holding devices. Rather, the wells 412 are used to allow receiving space for the probes when the probes are fully introduced between the elongated dielectric barrier members 402.

In operation, the microplate 400 is placed in, for example, a deck mounted wash station. In, for example, an automated microplate liquid handling instrumentation, the system performs an assay test. Then, at least the probe tips of the fluid handling device would need a cleaning. As such, the fluid handling device enters the wash station. A set of automated commands initiate and control the probes to be introduced to the microplate 400 proximate the elongated dielectric barrier members 402. At or about the same time, the AC voltage power source is initiated. Alternatively, the power source remains on during an extended period.

During the power-on phase, the probes are introduced to the dielectric members 402 of the microplate 400. At that time, dielectric barrier discharges are formed between the members 402 and the probes (see, e.g., FIG. 2). In an embodiment where the probes are hollow, the reactive and energetic components or species of the plasma are repeatedly aspirated into the probes, using the fluid handling devices' aspirating and dispensing capabilities. The aspiration volume, rate and frequency are determined by the desired amount of cleaning/sterilization required.

Any volatized contaminants and other products from the plasma may be vented through the bottom of the microplate 400 by coupling the bottom of the tray 410 to a region of negative pressure such as a modest vacuum. This vacuum may be in communication with the wells 412 and is capable of drawing down plasma and reactive byproducts through to the bottom of the device and into an exhaust manifold (not shown) of the cleaning station test set up.

In an embodiment, ions, excited and metastables species (corresponding emitted photons), and free radicals are found in the atmospheric pressure plasma and remain long enough to remove substantially all of the impurities and contaminates from the previous test performed by the fluid handling device's probes. These particle species remain longer (see FIG. 5) than the initial plasma formed from a DBD or microdischarge and are therefore effective in cleaning the probes in preparation for a next test as the initially formed plasma itself.

Figure 5:
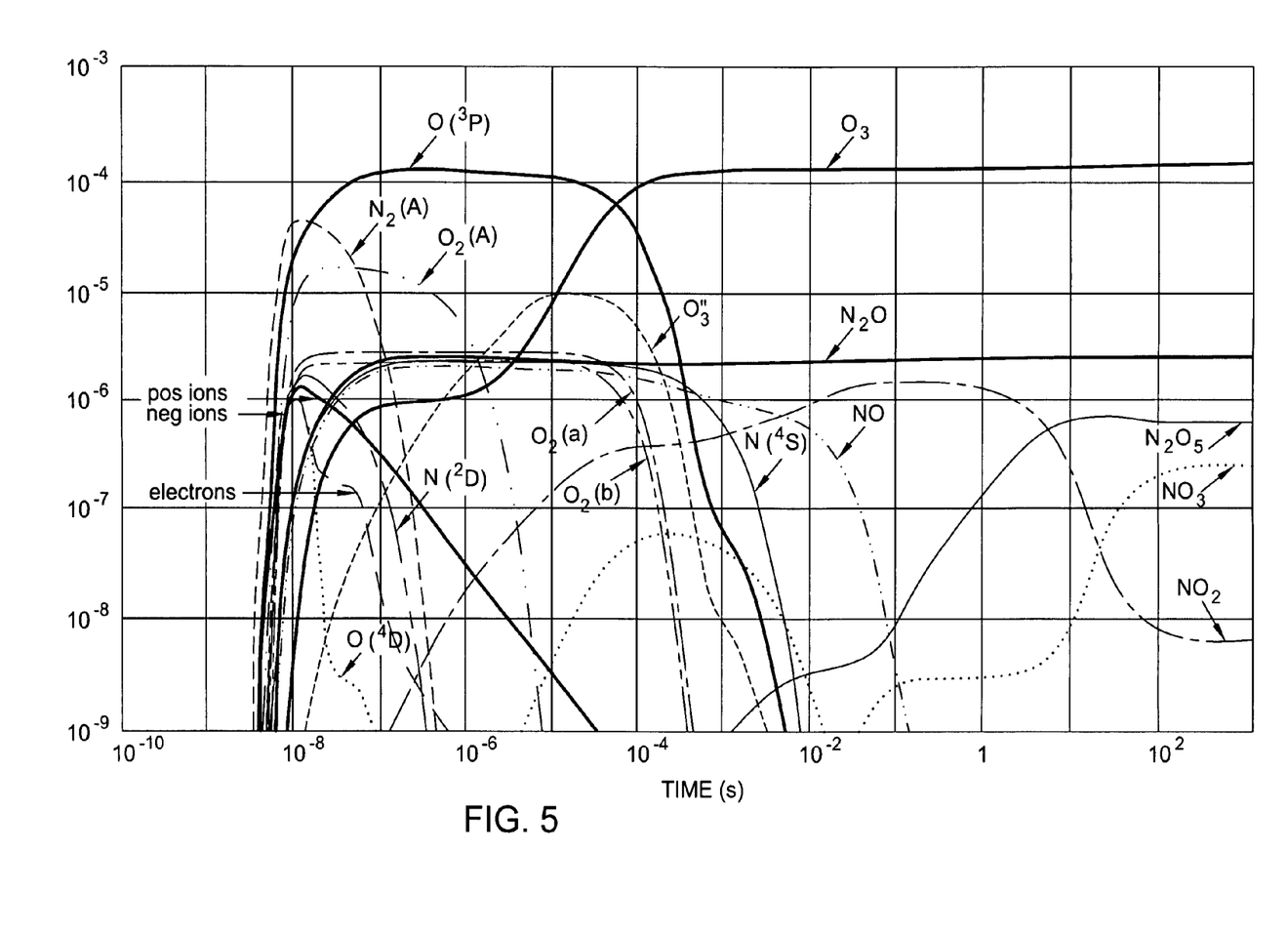
FIG. 5 represents a graph of the relative concentrations of different chemical and particle species of plasma in time after the initiation of a single microdischarge that forms atmospheric pressure plasma in air.

In particular, FIG. 5 represents a graph of the relative concentrations of different particle species in time after the initiation of a single microdischarge forming atmospheric pressure plasma in air. Metastables are represented by $N_2(A)$ and $N_2(B)$. Free radicals are represented by $O_3$, $O(^3P)$, $N(^4S)$ and NO. Free radicals and metastables are represented by $O(^1D)$ and $N(^2D)$. In non-equilibrium microdischarges, the fast electrons created by the discharge mechanism mainly initiate the chemical reactions in the atmospheric pressure plasma. The fast electrons can inelastically collide with gas molecules and ionize, dissociate, and/or excite them to higher energy levels, thereby losing part of their energy, which is replenished by the electric field. The resulting ionic, free radical, and excited species can then, due to their high internal energies or reactivities, either dissociate or initiate other reactions.

In plasma chemistry, the transfer of energy, via electrons, to the species that take part in the reactions must be efficient. This can be accomplished by a very short discharge pulse. This is what occurs in a microdischarge. FIG. 5 shows the evolution of the different particle species initiated by a single microdischarge in "air" (80% $N_2$, plus 20% $O_2$). The short current pulse of about 10 ns duration deposits energy in various excited levels of $N_2$ and $O_2$, some of which lead to dissociation and finally to the formation of ozone and different nitrogen oxides. After about 50 ns, most charge carriers have disappeared and the chemical reactions proceed without major interference from charge carriers and additional gas heating.

Figure 6:
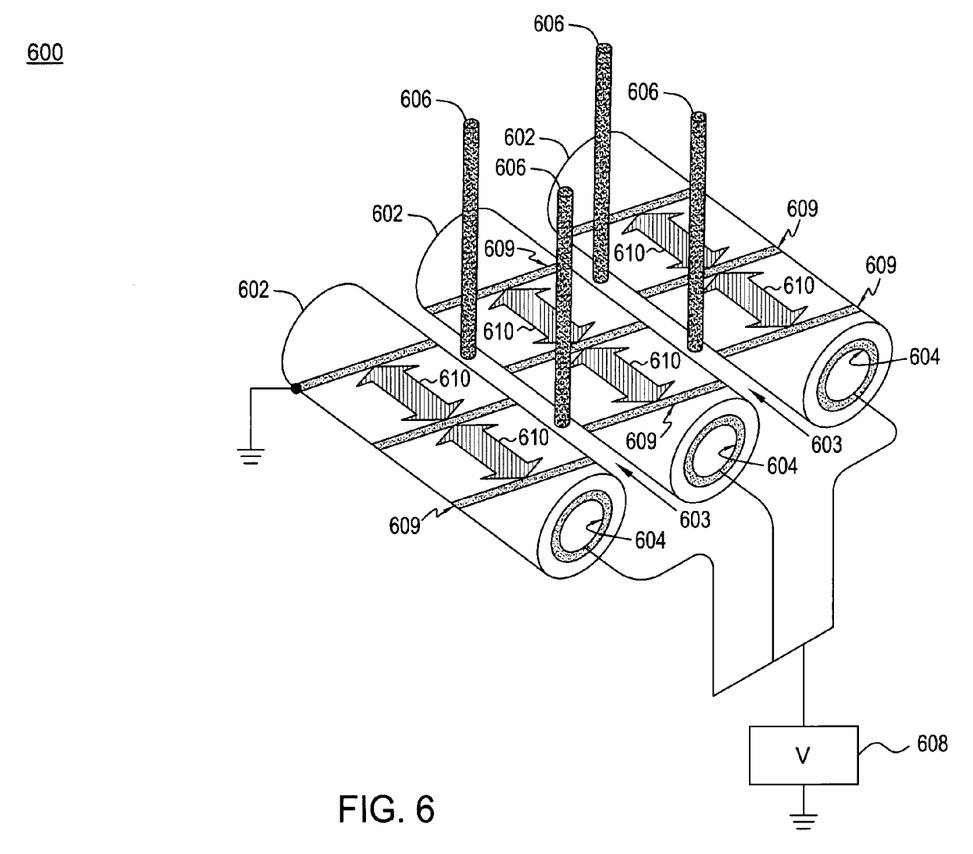
FIG. 6 is a top, partial perspective view of a plurality of probes being introduced to a plurality of elongated dielectric barrier members with coupled inner electrodes in accordance with another embodiment of the present invention.

FIG. 6 is a top, partial perspective view of a plurality of probes being introduced to a plurality of elongated dielectric barrier members with coupled inner electrodes in accordance with another embodiment of the present invention. Referring to FIG. 6, there is provided a cleaning device 600. The device 600 includes a plurality of elongated dielectric barrier members 602 arranged in a matrix or array, which lie in a plane. The members 602 are substantially regularly spaced apart from each other forming a gap 603 between adjacent members 602. Each dielectric barrier member 602 includes an inner electrode 604 extending within, and substantially along the length of, respective elongated dielectric barrier members 602. The inner electrodes 604 are electrically coupled to a voltage supply 608 similar to that described herein.

In addition, each dielectric barrier member 602 includes on its surface a secondary ground grid 609. Here, the ground grid 609 is in the form of a conductive spiral, coupled to the surface of each dielectric barrier member 602 and to ground.

In this manner, plasma will extend along the surface of each elongated dielectric barrier members 602 as designated by large arrows 610. In this particular embodiment, conductive, electrically isolated, and non-conductive probes 606 can be treated by the plasma formed between spacing of the grid 609 because plasma formation is not necessarily dependent on the probe being conductive. Rather, plasma is formed independent of the probes on the surface of the members 602.

A plurality of probes 606 are shown extending into open spaces or gaps 603 between the plurality of dielectric barrier members 602. In one embodiment, the probes 606 are part of a fluid handling device. As such, the probes 606 are attached to and extend from a fluid handling device (not shown), which may be part of a microtiter plate test bed set up. In other embodiments, the probes 606 may be any form of an object that would benefit from plasma cleaning.

In the embodiment shown in FIG. 6, the elongated dielectric barrier members 602 are made of any type of material capable of providing a surface for a dielectric barrier discharge of atmospheric pressure plasma (described herein). Dielectric barrier material useful in this embodiment of the present invention includes, but is not limited to, ceramic, glass, plastic, polymer epoxy, or a composite of one or more such materials, such as fiberglass or a ceramic filled resin (available from Cotronics Corp., Wetherill Park, Australia). The various types of materials discussed with respect to previous figures apply here as well.

The inner electrode 604 may comprise any conductive material, including metals, alloys and conductive compounds as described herein with respect to the other figures. The inner electrodes 604 of the present invention may be formed using any method known in the art, including those mentioned herein in connection with the other figures.

In one use of this embodiment of the present invention, the secondary ground grid is conductive and made of formable conductive material described herein with respect to the inner electrode. For example, the ground grid can be a separate conductive wire or conductive paint deposited on the members, and the like, as described previously. The probes 606 are part of the fluid handling device and are introduced in the gap 603, i.e., proximate the elongated dielectric barrier members 602 of the plasma cleaning device 600. In this embodiment, the probe 606 can either conductive or non-conductive. If conductive, it is made of conductive material similar to that material described above in connection with the inner electrode 604. In other embodiments, as described below, the probe is non-conductive and can be made of any non-conductive material known to one of ordinary skill in the art.

In addition to the above operation of introducing the probes 606 between the elongated dielectric barrier members 602, similar to FIG. 1B, the probes 606 can be introduced proximate the elongated dielectric barrier members 602. That is, each probe 606 may be introduced proximate one or more elongated dielectric barrier members 602. When each probe 606 is introduced proximate two elongated dielectric barrier members 602, the probe 606 may be introduced proximate or between the two elongated dielectric barrier members 602.

Figure 7:
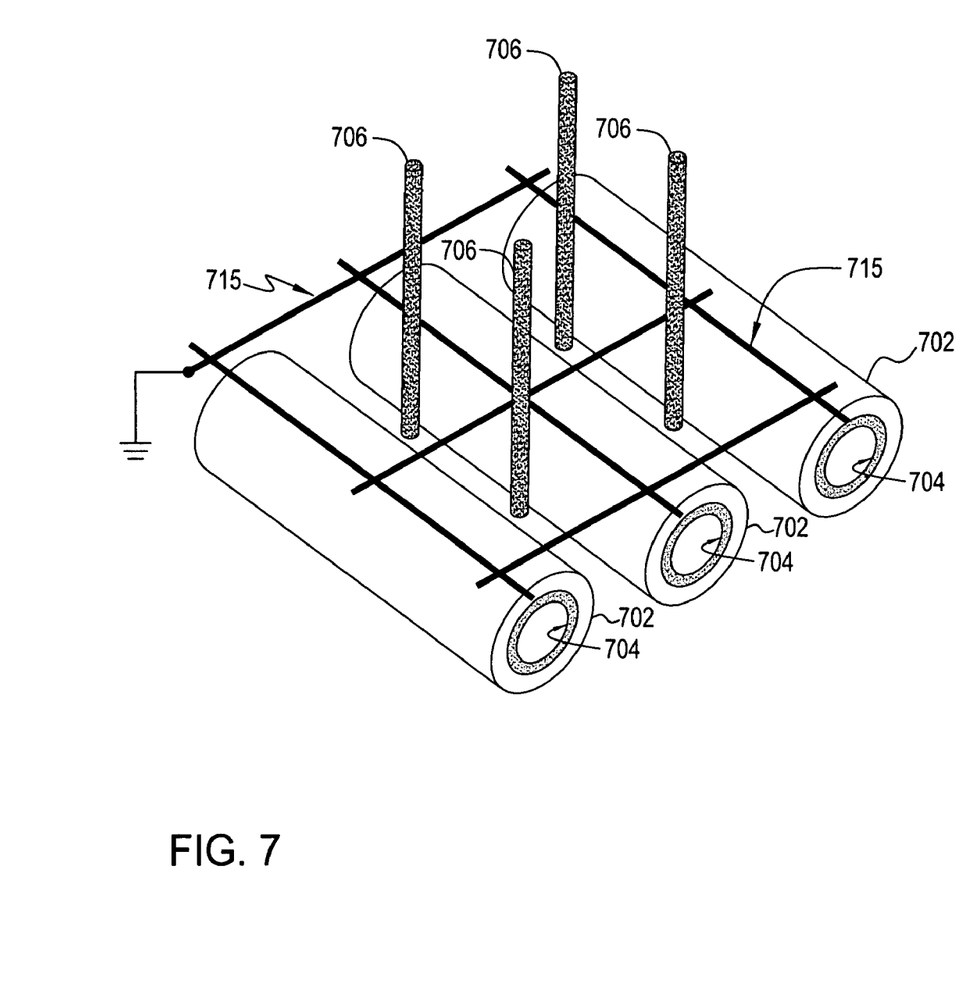
FIG. 7 is a top, partial perspective view of a plurality of probes being introduced to a plurality of elongated dielectric barrier members with coupled inner electrodes in accordance with yet another embodiment of the present invention.

FIG. 7 is a top, partial perspective view of a plurality of probes 706 being introduced to a plurality of elongated dielectric barrier members 702 with coupled inner electrodes 704 in accordance with yet another embodiment of the present invention. Similar to FIG. 6, this embodiment includes a secondary ground plane 715. In this embodiment, the ground plane 715 is in the form of a conductive mesh positioned either above or below the elongated dielectric barrier members 702. FIG. 7 depicts the ground plane 715 above the members for clarity purposes but it is to be understood that a ground plane below the members 702 is also contemplated by this embodiment of the present invention. In addition ground planes above and below are contemplated and within the scope of the present invention.

Similar to the earlier embodiments, this embodiment includes elongated dielectric barrier members, inner electrodes, probes and secondary ground grids as described hereinabove. In addition, although not shown, the inner electrodes are electrically coupled to a voltage source similar to that shown with respect to FIG. 6 described. With the added conductive mesh secondary ground plane 715, plasma will form between the ground plane portions 715 and the elongated dielectric barrier members 702. Therefore, the probes 706 can be either conductive or non-conductive as herein described.

Figure 8:
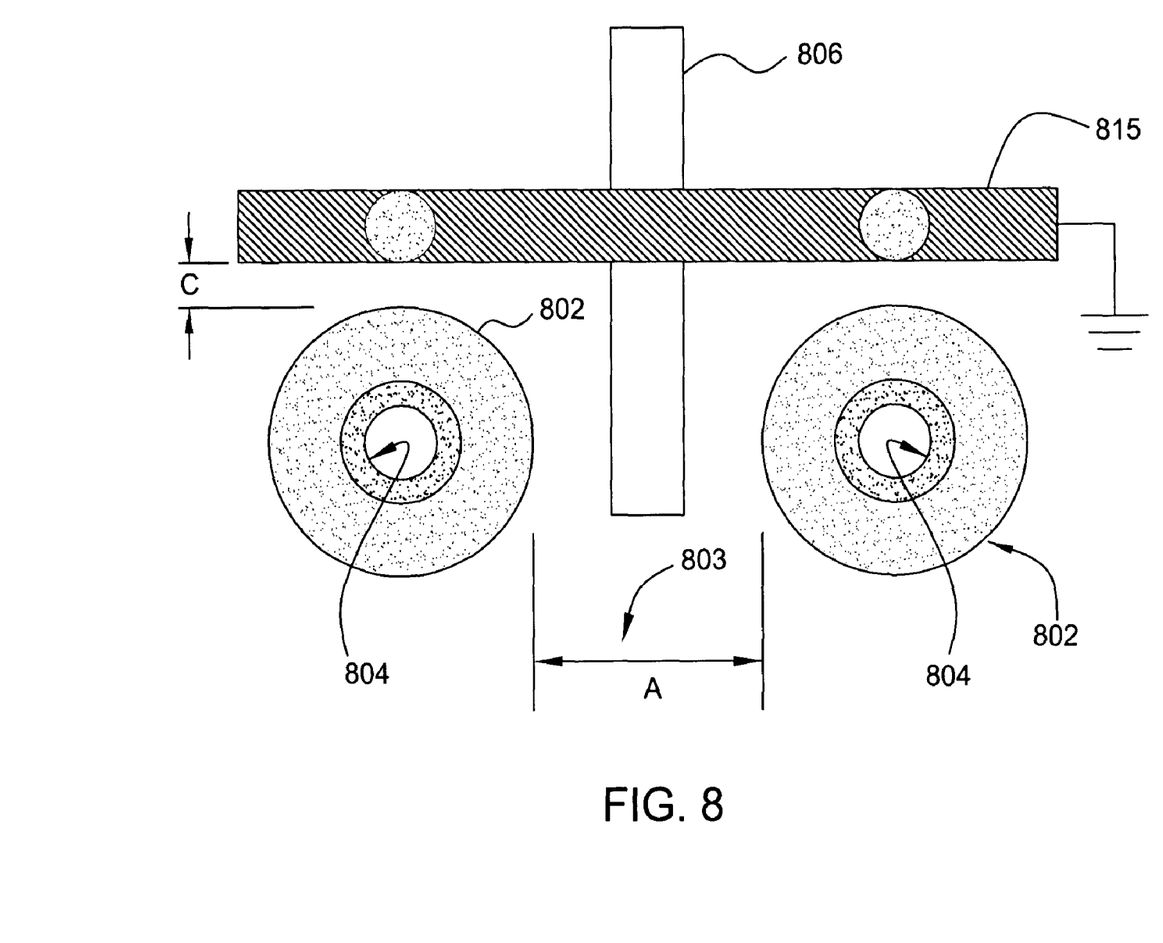
FIG. 8 is a partial, cross sectional view of the embodiment shown in FIG. 7.

FIG. 8 is a partial, cross sectional view of the embodiment shown in FIG. 7, depicting one example of the geometry and relationship among components of this embodiment of the present invention. The elongated dielectric barrier member 802 may comprise, for example, an elongated hollow tube with a hollow inner electrode 804 extended substantially the length of the elongated dielectric barrier member 802. Alternatively, the elongated dielectric barrier member 802 may comprise other than a tube, such as a solid with a solid inner electrode 804. The elongated dielectric barrier member 802 may be formed of different shapes as well. For example, and not in any way limiting, the shape of the elongated dielectric barrier member 802 may be tubular, circular, square, rectangular, oval, polygonal, triangular, trapezoidal, rhombus and irregular. If tubular, each elongated dielectric barrier member is about 2 mm in diameter and about 75 to about 120 mm long.

The elongated dielectric barrier members 802 are placed adjacent one another, defining a plane. The secondary ground plane 815 is shown on top of the elongated dielectric barrier members 802 but would be within the scope of this embodiment if they were below the members 802. The members 802 are spaced at regular intervals and form a gap 803, designated as spacing A. Alternatively, the members 802 can be staggered in a non-planar arrangement with respect to one another. The spacing A is sized to allow at least a portion of each of the plurality of probes 806 to be introduced proximate or between the elongated dielectric barrier members. The gap 803 or spacing A can approach zero, provided there is a sufficient gap to allow gas such as air to flow through the elongated dielectric barrier members 802. Spacing A or gap 803 can range from about 0 mm to about 10 mm. The spacing A or gap 803 may also range from about 2 mm to about 9.5 mm. In one embodiment, the spacing A is about 9 mm. In another embodiment, the spacing A is about 4.5 mm. In yet another embodiment, the spacing A is about 2.25 mm. In addition, spacing C is provided. Spacing C is size to provide for the production of plasma between the ground plane 815 and the elongated dielectric barrier member 802 for a given applied voltage on inner electrodes 804. Typically, spacing C ranges from about 0.0 mm to about 1 cm. It may also range from about 0.5 mm to about 2 mm.

Figure 9:
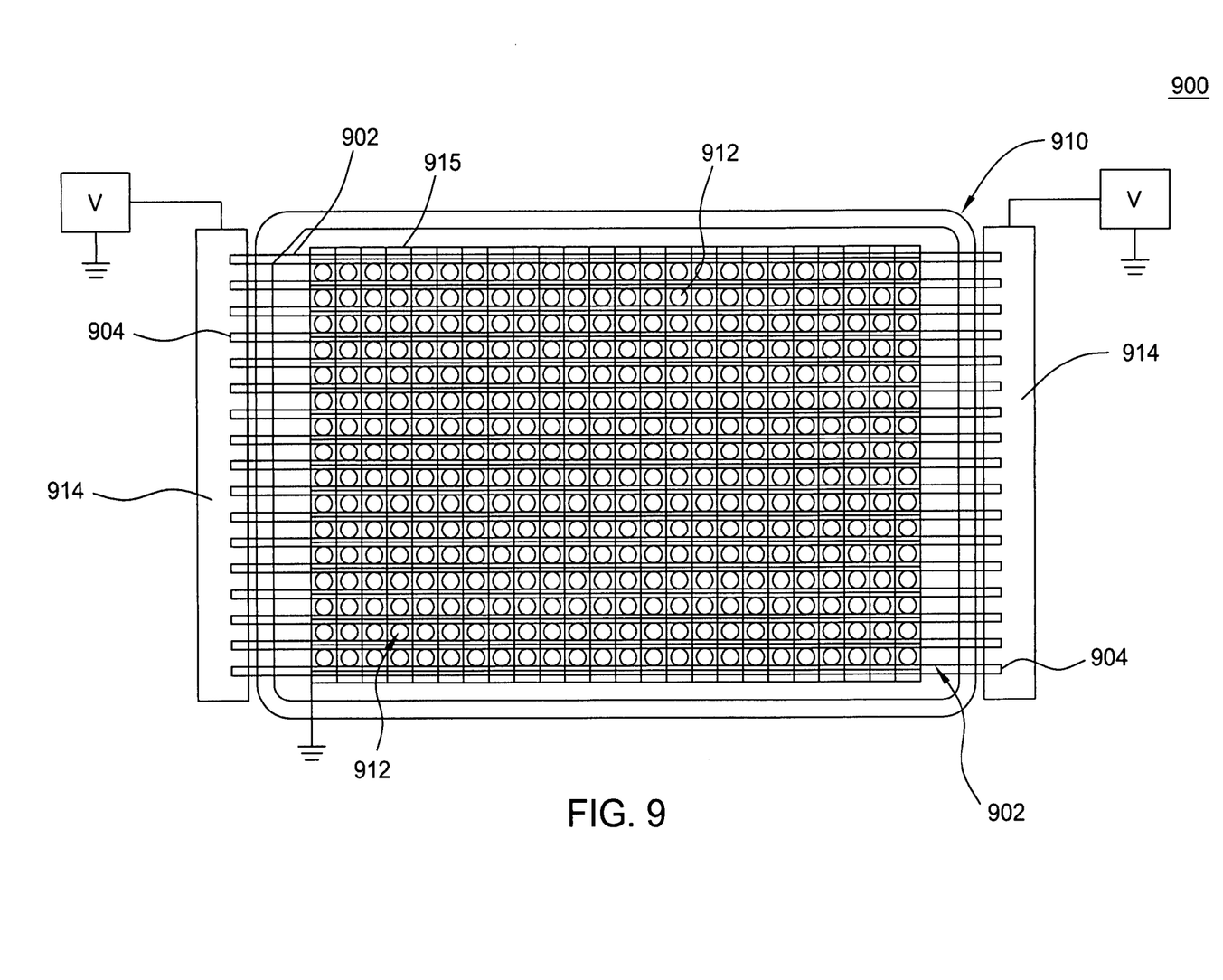
FIG. 9 is a top plan view of a matrix or array of the devices of FIG. 6 or 7 showing the plurality of elongated dielectric barrier members arranged in a microtiter plate format.

FIG. 9 is a top plan view of a matrix or array of a device including a ground plane similar to that shown in FIG. 7, depicting the plurality of elongated dielectric barrier members arranged in a microtiter plate format 900. The microtiter plate format may be sized to accommodate about 96 openings for receiving a plurality of fluid handling probes. Alternatively, the microtiter plate is sized to accommodate about 384 openings for receiving a plurality of probes as depicted above. As an alternative, the wells and the pitch between rows of wells of the microtiter plate are sized to accommodate about 1536 openings for receiving a plurality of probes.

The microplate 900 has been equipped with an embodiment of the present invention having a ground plane or grid. Situated in rows on the top surface of the microplate 900 and between the wells 912 are a plurality of elongated dielectric barrier members 902 similar to those described hereinabove. The inner electrodes 904 of the elongated dielectric barrier members 902 are electrically coupled to the AC voltage source through bus bars or contact planes 914 of the cassette 910. A meshed secondary ground plane 915 is disposed a spacing C from the elongated dielectric barrier members 902 on the top of the members. This secondary ground plane 915 is grounded with respect to the AC voltage source.

Similar to the microplate discussed herein, the elongated dielectric barrier members 902 are each spaced apart in this particular embodiment a pitch of about 4.5 mm. In alternative embodiments, where the well count is 96, the members 902 are spaced apart a pitch of about 9 mm. In yet another embodiment, where the wells 912 numbered 1536, the pitch is about 2.25 mm. The wells 912 are used to allow receiving space for the probes (not shown) when the probes are fully introduced between the elongated dielectric barrier members 902 and within the secondary ground grid 915.

In operation, the microplate 900 is placed in, for example, a deck mounted wash station. In, for example, an automated microplate liquid handling instrumentation, the system performs an assay test. Then, at least the probe tips of the fluid handling device would need a cleaning. As such, the fluid handling device enters the wash station. A set of automated commands initiate and control the probes to be introduced to the microplate 900 proximate the elongated dielectric barrier members 902. At or about the same time, the AC voltage power source is initiated. Alternatively, the power source remains on during an extended period.

During the power-on phase, the probes are introduced to the dielectric members 902 of the microplate 900. At that time, dielectric barrier discharges are formed between the members 902 and the secondary ground plane 915. In an embodiment where the probes are hollow, the reactive and energetic components or species of the plasma are repeatedly aspirated into the probes, using the fluid handling devices' aspirating and dispensing capabilities. The aspiration volume, rate and frequency are determined by the desired amount of cleaning/sterilization required.

Any volatized contaminants and other products from the plasma may be vented through the bottom of the microplate 900 by coupling the bottom of the tray 910 to a region of negative pressure such as a modest vacuum. This vacuum may be in communication with the wells 912 and is capable of drawing down plasma and reactive byproducts through to the bottom of the device and into an exhaust manifold (not shown) of the cleaning station test set up.

While the foregoing is directed to embodiments of the present invention, other and further embodiments of the invention may be devised without departing from the basic scope thereof, and the scope thereof is determined by the claims that follow.

What is claimed is:

1. An apparatus for cleaning objects using plasma, comprising:
   a microplate provided with
   a plurality of elongated dielectric barrier members arranged adjacent each other defining a gap therebetween;
   a plurality of electrodes, each contained within, and extending substantially along the length of, respective ones of the elongated dielectric barrier members; and a ground member proximate the plurality of elongated dielectric barrier members;

wherein said ground member defines at least one gap aligned with the gap between each adjacent elongated dielectric barrier member suitable for receiving at least a portion of the objects to be cleaned.

2. The apparatus of claim 1, wherein the objects comprise a plurality of probes, the probes being arranged and configured to be introduced proximate the elongated dielectric barrier members and ground member.

3. The apparatus of claim 2, further comprising a voltage source electrically coupled to the electrodes for producing a dielectric barrier discharge between the elongated dielectric barrier members and the ground member, whereby plasma is formed to clean at least a portion of the probes.

4. The apparatus of claim 2, wherein the elongated dielectric barrier members are arranged to define a plane.

5. The apparatus of claim 4, wherein the elongated dielectric barrier members are spaced apart from each other at substantially regular intervals to define predetermined gaps therebetween.

6. The apparatus of claim 5, wherein the predetermined gaps are sized to allow at least a portion of the probes to be introduced between the elongated dielectric barrier members and proximate the ground member.

7. The apparatus of claim 1, wherein the ground member comprises a secondary ground grid.

8. The apparatus of claim 1, wherein the ground member comprises a plurality of conductive spirals, each arranged to be coupled to the surface of one of said elongated dielectric barrier members.

9. The apparatus of claim 8, wherein the conductive spiral is deposited on each respective one of the elongated dielectric barrier members.

10. The apparatus of claim 8, wherein the conductive spiral is a discrete component secured on each of the elongated dielectric barrier members.

11. The apparatus of claim 7, wherein the secondary ground grid comprises a conductive mesh positioned proximate the elongated dielectric barrier members.

12. The apparatus of claim 11, wherein the conductive mesh is positioned a spacing C from the surface of the elongated dielectric barrier members, where spacing C is from about 0.0 mm to about 1 cm.

13. The apparatus of claim 12, wherein spacing C is from about 0.5 mm to about 2 mm.

14. The apparatus of claim 2, wherein the probes are introduced proximate the elongated dielectric barrier members.

15. The apparatus of claim 1, wherein the elongated dielectric barrier members and ground plane are arranged so as to form orderly rows defining a predetermined gap between adjacent barrier members.

16. The apparatus of claim 1, wherein the shape of the elongated dielectric barrier members is selected from the group consisting of tubular, circular, square, rectangular, oval, polygonal, triangular, trapezoidal, rhombus and irregular.

17. The apparatus of claim 1, wherein the elongated dielectric barrier members are arranged in a non-planar configuration.

18. An apparatus for cleaning objects using plasma, comprising: a microplate further provided with a plurality of elongated dielectric barrier members arranged adjacent each other in a microtiter plate matrix format; a plurality of electrodes, each contained within, and extending substantially along the length of, respective ones of the elongated dielectric barrier members; and a ground member proximate the plurality of elongated dielectric barrier members.

19. The apparatus of claim 15, wherein said orderly rows define gaps between adjacent barrier members that correspond in location to wells of a microtiter plate matrix format.

* * * * *